US005432182A

United States Patent [19]
Ife et al.

[11] Patent Number: 5,432,182
[45] Date of Patent: Jul. 11, 1995

[54] COMPOUNDS SUBSTITUTED QUINOLINE DERIVATIVES

[75] Inventors: Robert J. Ife; Colin A. Leach, both of Hertfordshire, England

[73] Assignee: SmithKline Beecham Intercredit B.V., Rotterdam, Netherlands

[21] Appl. No.: 827,790

[22] Filed: Jan. 29, 1992

Related U.S. Application Data

[63] Continuation-in-part of Ser. No. 314,726, Feb. 23, 1989, Pat. No. 5,089,504.

[30] Foreign Application Priority Data

Jan. 29, 1991 [GB] United Kingdom ............... 9101918
Jan. 29, 1991 [GB] United Kingdom ............... 9101919

[51] Int. Cl.$^6$ ...................... A61K 31/47; A01N 43/40
[52] U.S. Cl. ................... 514/278; 514/206; 514/249
[58] Field of Search ................ 514/278, 249, 206

[56] References Cited

U.S. PATENT DOCUMENTS 4,343,804 8/1982 Munson, Jr. et al. ............. 424/258

OTHER PUBLICATIONS

Ife, et al. Chemical Abstracts vol. 112(17)158,073s Apr. 23, 1990.
Ife, et al. "Chemical Abstracts" vol. 117(23) 233,869g 1992.
Grundler, et al. "Chemical Abstracts" vol. 119(21) 225,851d Nov. 29, 1993.

*Primary Examiner*—Werren B. Lone
*Attorney, Agent, or Firm*—Dara L. Dinner; Stephen Venetianer; Edward T. Lentz

[57] ABSTRACT

Substituted 4-aminoquinazoline derivatives which are inhibitors of gastric acid secretion. A compound of the invention are the salts of strong acids of 3-butyryl-4-(2-methylphenylamino)-8-(hydroxymethyl)quinoline.

10 Claims, No Drawings

COMPOUNDS SUBSTITUTED QUINOLINE DERIVATIVES

RELATED APPLICATIONS

This application is a continuation in part application of U.S. Ser. No. 07/314,726, filed 23 Feb. 1989, now U.S. Pat. No. 5,089,504, issued on 18 Feb. 1992.

The present invention relates to novel substituted quinoline derivatives, processes for their preparation, intermediates useful in their preparation, pharmaceutical compositions containing them and their use in therapy.

Substituted quinoline derivatives that inhibit gastric acid secretion are known in the art. For example, U.S. Pat. No. 4,343,804 and EP 259174-A disclose series of 4-phenylaminoquinoline compounds in which the quinoline ring is substituted by, inter alia, one or more alkyl, phenyl, alkoxy, alkylthio or halogen groups. The present invention relates to substituted quinoline derivatives comprising a novel range of substituents on the quinoline ring which have also been found to be useful in the inhibition of gastric acid secretion.

Accordingly, the present invention provides, in a first aspect, a compound of structure (I):

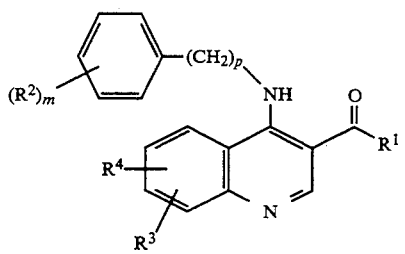

in which
R$^1$ is hydrogen, C$_{1-6}$alkyl, C$_{1-6}$alkoxy, C$_{1-6}$alkoxyC$_{1-6}$-alkyl, C$_{3-6}$cycloalkyl, C$_{3-6}$cycloalkylC$_{1-6}$alkyl, phenyl, phenylC$_{1-6}$alkyl, the phenyl groups being optionally substituted;
R$^2$ is hydrogen, C$_{1-6}$alkyl, C$_{1-6}$alkoxy, amino, C$_{1-6}$alkylthio, halogen, cyano, hydroxy, carbamoyl, carboxy, C$_{1-6}$alkanoyl or trifluoromethyl;
m is 1, 2 or 3;
p is 0 to 4;
R$^3$ is hydroxyC$_{1-6}$alkyl, polyhydroxyC$_{1-6}$alkyl, C$_{1-6}$alkoxyC$_{1-6}$alkyl, hydroxyC$_{1-6}$alkoxy, polyhydroxyC$_{1-6}$alkoxy, C$_{1-6}$alkoxyC$_{1-6}$alkoxy or hydroxyC$_{1-6}$alkoxyC$_{1-6}$alkoxy; and
R$^4$ is hydrogen, hydroxy, C$_{1-6}$alkyl, or C$_{1-6}$alkoxy;
or a salt thereof.

Suitably, R$^1$ is hydrogen, C$_{1-6}$alkyl, C$_{1-6}$alkoxy, C$_{1-6}$alkoxyC$_{1-6}$alkyl, C$_{3-6}$cycloalkyl, C$_{3-6}$cycloalkylC$_{1-6}$alkyl, phenyl or phenylC$_{1-6}$alkyl, the phenyl groups being optionally substituted. Preferably R$^1$ is C$_{1-6}$alkyl, C$_{1-6}$alkoxy, C$_{3-6}$cycloalkyl or C$_{3-6}$cycloalkylC$_{1-6}$alkyl. Most preferably R$^1$ is C$_{1-6}$alkyl, in particular ethyl, i-propyl or n-propyl.

Suitably R$^2$ is hydrogen, C$_{1-6}$alkyl, C$_{1-6}$alkoxy, amino, C$_{1-6}$alkylthio, halogen, cyano, hydroxy, carbamoyl, carboxy, C$_{1-6}$alkanoyl or trifluoromethyl. Preferably R$^2$ is a single substituent other than hydrogen in the 2-position of the phenyl ring or two substituents other than hydrogen in the 2 and 4-positions of the phenyl ring.

More preferably, R$^2$ is a C$_{1-6}$alkyl or C$_{1-6}$alkoxy group, for example, a methyl or methoxy group in the 2-position of the ring or a C$_{1-6}$alkyl or C$_{1-6}$alkoxy group in the 2-position in combination with a halogen substituent, in particular fluoro, in the 4-position of the ring.

Suitably m is 1, 2 or 3; preferably m is 1 or 2.

Suitably p is 0, 1, 2, 3 or 4; preferably p is 0 or 1; most preferably p is 0.

Preferably R$^3$ is in the 8-position of the quinoline ring.

Suitably R$^3$ is hydroxyC$_{1-6}$alkyl, polyhydroxy-C$_{1-6}$alkyl, C$_{1-6}$alkoxyC$_{1-6}$alkyl, hydroxyC$_{1-6}$alkoxy, polyhydroxyC$_{1-6}$alkoxy, C$_{1-6}$alkoxyC$_{1-6}$alkoxy or hydroxyC$_{1-6}$alkoxyC$_{1-6}$alkoxy. Preferably, R$^3$ is hydroxyC$_{1-6}$alkyl, hydroxyC$_{1-6}$alkoxy or C$_{1-6}$alkoxy-C$_{1-6}$alkoxy; most preferably R$^3$ is hydroxy C$_{1-6}$alkoxy or C$_{1-6}$alkoxyC$_{1-6}$-alkoxy, in particular hydroxyethoxy or methoxyethoxy.

Suitably R$^4$ is hydrogen, hydroxy, C$_{1-6}$alkyl or C$_{1-6}$alkoxy; preferably R$^4$ is hydrogen.

C$_{1-6}$alkyl groups (either alone or as part of another group) can be straight or branched.

Phenyl C$_{1-6}$alkyl groups include for example the benzyl, phenylethyl, phenylpropyl and phenylbutyl groups; and groups in which the alkyl portion is branched e.g. 1-methylbenzyl.

Substituted phenyl and phenyl C$_{1-6}$alkyl groups R$^1$ include, for example, phenyl groups substituted by 1 to 3 substituents as hereinbefore described as R$^2$. Such substituent groups include hydrogen, C$_{1-6}$alkyl, C$_{1-6}$alkoxy, amino, C$_{1-6}$alkylthio, halogen, cyano, hydroxy, carbamoyl, carboxy, C$_{1-6}$alkanoyl or trifluoromethyl.

HydroxyC$_{1-6}$alkyl groups include, for example, hydroxymethyl, 2-hydroxyethyl groups and groups in which the hydroxy group is other than at the end of the chain e.g. 1-hydroxyethyl.

PolyhydroxyC$_{1-6}$alkyl groups are alkyl groups which are substituted by more than a single hydroxy group, for example, a 2,3-dihydroxypropyl or 2,3-dihydroxybutyl group.

C$_{1-6}$AlkoxyC$_{1-6}$alkyl groups include for example, methoxymethyl and methoxyethyl groups.

HydroxyC$_{1-6}$alkoxy groups include for example, 2-hydroxy propyloxy groups of structure —OCH$_2$CH(OH)CH$_3$.

PolyhydroxyC$_{1-6}$alkoxy groups include alkoxy groups which are substituted by more than a single hydroxy group, for example a 1,3-dihydroxybutyloxy group of structure OCH$_2$CH(OH)CH$_2$CHOH.

C$_{1-6}$AlkoxyC$_{1-6}$alkoxy groups include in particular methoxyethoxy groups.

HydroxyC$_{1-6}$alkoxyC$_{1-6}$alkoxy groups include for example 2-hydroxyethoxyethoxy groups.

It will be appreciated that compounds of structure (I) in which one or more of R$^1$ to R$^4$ is a C$_{3-6}$alkyl group (either alone or as part of another group for example a benzyl or phenethyl group) may contain an asymmetric centre due to the presence of the C$_{3-6}$alkyl group. Similarly, compounds of structure (I) in which R$^3$ is a secondary hydroxy group such as a —OCH$_2$CH(OH)CH$_3$ group will also contain an asymmetric centre. Such compounds will exist as optical isomers (enantiomers). Both the pure enantiomers, racemic mixtures (50% of each enantiomer) and unequal mixtures of the two am included within the scope of the present invention. Further, all diastereomeric forms possible (pure enantiomers and mixtures thereof) are within the scope of the invention.

Compounds of structure (I) can form salts, in particular pharmaceutically acceptable acid addition salts with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as for example, citric, maleic or fumaric acids.

Preferred salts are those formed by reaction of a compound of structure (I) with a strong acid.

As used herein, the term strong acid shall be taken to mean an acid with a pka of less than about 4.0. The nature of such acids will be apparent to those skilled in the art and include, for example, mineral acids such as hydrochloric acid, and sulphonic acids such as alkyl sulphonic acids, in particular methane sulphonic acid.

Particularly preferred salts are those formed by reaction of a strong acid as hereinbefore defined with the compound of example 10, that is to say, 3-butyryl-4-(2-methylphenylamino)-8-(2-hydroxyethoxy)quinoline. Specifically preferred are salts formed by reaction with hydrochloric acid or methane sulphonic acid, with the compound of example 10, that is to say 3-butyryl-4-(2-methylphenylamino)-8-(2-hydroxyethoxy)-quinoline hydrochloride and 3-butyryl-4-(2-methylphenylamino)-8-(2-hydroxyethoxy)-quinoline mesylate.

It has been found that these salts namely the hydrochloride and mesylate salts of the compound of Example 10, exhibit exceptionally fast intrinsic dissolution rates when compared to the free base compounds. Thus, whereas the free bases have poor dissolution rates and, as such, may be expected in vivo to exhibit poorly reproducible bioavailability (and so be less effective therapeutically), the salts are expected to exhibit much more consistent bioavailability (since their dissolution rates are far more favourable) and thus prove more effective per given dose and prove more reliably effective per given dose on administration to patients.

In a further aspect, the present invention provides a process for the preparation of a compound of structure (I) which comprises (a) reaction of a compound of structure (II) with a compound of structure (III):

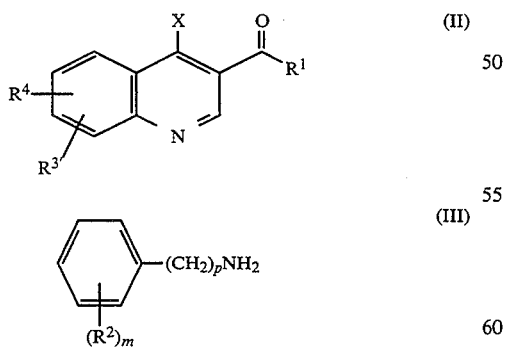

in which $R^1$, $R^2$, $R^4$, m and p are as described for structure (I); $R^{3'}$ is an optionally protected group $R^3$ and X is a group displaceable by an amine;

(b) for compounds of structure (I) in which p is 1 to 4 reaction of a compound of structure (IV) with a compound of structure (V):

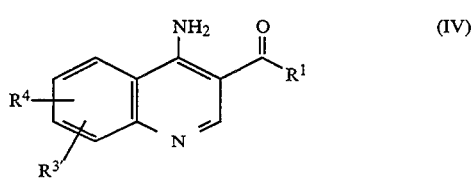

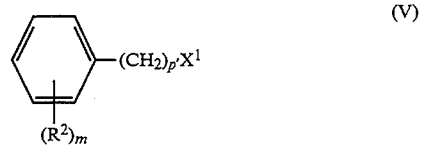

in which $R^1$, $R^2$, $R^4$ and m are as described for structure (I); $R^{3'}$ is as described for structure (II); p' is 1 to 4; and $X^1$ is a leaving group;

(c) reduction of a compound of structure (VI):

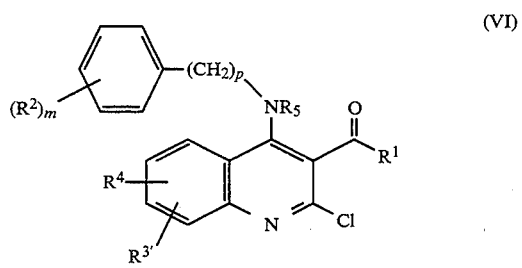

in which $R^1$, $R^2$, m, p and $R^4$ are as described for structure (I); $R^{3'}$ is as described for structure (II); and $R^5$ is hydrogen or a nitrogen protecting group;

(d) alkylation of a compound of structure (VII):

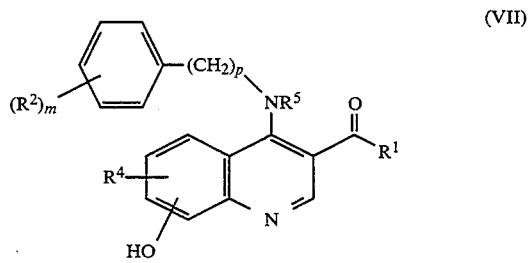

in which $R^1$, $R^2$, m, p and $R^4$ are as described for structure (I); and $R^5$ is as described for structure (VI);

(e) for compounds of structure (I) in which $R^1$ is other than $C_{1-6}$alkoxy, oxidation of a compound of structure (VIII):

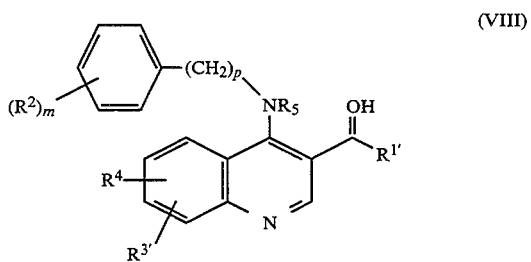

in which $R^2$, m, p and $R^4$ are as described for structure (I); $R^{1'}$ is a group $R^1$ other than $C_{1-6}$alkoxy and $R^{3'}$ and $R^5$ are as described for structure (VI); and thereafter if desired, removing any protecting groups;
converting a group $R^1$ into another group $R^1$;
converting one group $R^3$ into another group $R^3$;
forming a salt.

Suitable groups X displaceable by an amine, include for example, halo, aryl or alkylsulphonates, for example, toluene-p-sulphonate or methane sulphonate, alkylthio, alkylsulphonyl, alkylsulphinyl, alkoxy or aryloxy.

Preferably X is a halo moiety, for example, chloro or bromo, or an aryloxy group such as phenoxy.

Suitable leaving groups $X^1$ will be apparent to those skilled in the art and include for example a halo moiety, preferably chloro or bromo.

Suitable nitrogen protecting groups $R^5$ and groups to protect the hydroxy group(s) in $R^{3'}$ will be apparent to those skilled in the art for example as described in "Protective Groups in Organic Synthesis" T. W. Greene, 1981 (Wiley).

Suitable protected groups $R^3$ are those in which the hydroxy group(s) are in protected form. Such groups will be apparent to those skilled in the art as described in the above-noted reference, for example acylated groups such as acetyl and benzoyl, or if appropriate acetonides.

The reaction between compounds of structure (II) and compounds of structure (III) is carried out in an organic solvent at a temperature of between ambient and reflux temperature of the solvent used. Suitable solvents include, for example, tetrahydrofuran, dioxan or anisole. Preferably the reaction is carried out at reflux temperature in dioxan as a solvent.

The reaction between compounds of structure (IV) and compounds of structure (V) is carried out in an inert organic solvent at a temperature of between ambient and reflux temperature of the solvent used, preferably in the presence of a strong base. Suitable solvents include for example, dimethyl sulphoxide or tetrahydrofuran. Suitable bases include for example, lithium diisopropylamide or dimsyl sodium.

The reduction of a compound of structure (VI) is carried out by for example hydrogenation, over a noble metal catalyst in a suitable solvent. Suitably the reaction is carried out over a palladium on carbon catalyst in ethanol as a solvent.

The compounds of structure (VI) can be prepared from the corresponding compounds of structure (IX)

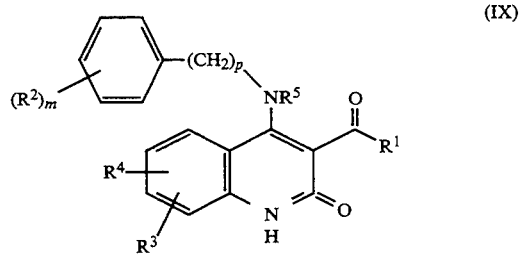

(IX)

in which $R^1$, $R^2$, $R^3$, $R^4$, $R^5$, m, p and n are as hereinbefore described, by reaction with, for example, phosphorus oxychloride.

The alkylation of a compound of structure (VII) is carried out in the presence of an alkylating agent in a suitable organic solvent preferably at reflux temperature of the solvent used in the presence of a strong base.

Suitable alkylating agents include, for example an epoxide, for example epichlorohydrin, chlorohydroxyalkane or an alkoxyalkyl benzene sulphate. Suitable strong bases and solvents include, for example, potassium t-butoxide in tetrahydrofuran, or potassium carbonate in acetone.

The oxidation of a compound of structure (VIII) is carried out in a suitable solvent in the presence of an oxidising agent. Suitable oxidising agents include, for example, manganese dioxide or chromium trioxide.

Suitable interconversions of groups $R^1$ will be apparent to those skilled in the art, for example compounds of structure (I) in which $R^1$ is $C_{2-6}$alkyl, $C_{3-6}$cycloalkyl$C_{2-6}$alkyl or optionally substituted phenyl$C_{2-6}$alkyl can be prepared by alkylation of the following compounds of structure (IA):

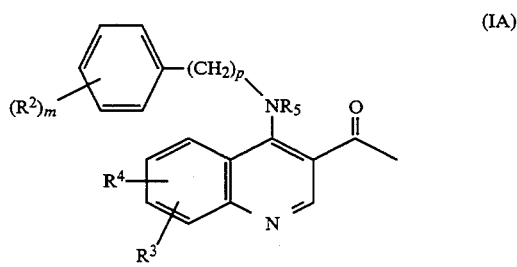

(IA)

in which $R^2$, $R^3$, $R^4$, m and p are as described for structure (I); and $R^5$ is as described for structure (IV).

The alkylation of compounds of structure (IA) is carried out in the presence of an alkylating agent in a suitable organic solvent at a temperature of between ambient and reflux temperature of the solvent used in the presence of a strong base. Suitable alkylating agents include, for example alkyl or aralkyl halides such as methyl or benzyl iodide and dialkyl sulphates such as dimethyl or diethylsulphate. Suitable strong bases include, for example, sodium hydride, lithium diisopropylamide or dimsyl sodium (the sodium salt of dimethyl sulphoxide). Subsequent removal of any protecting groups present affords the desired compounds of structure (I).

The intermediates of structure (II), (IV), (VI), (VII), (VIII) and (IX) can be prepared by standard techniques.

The intermediates of structure (III) and (V) are commercially available or can be prepared by standard techniques.

The compounds of structure (I) and their pharmaceutically acceptable salts exert an anti-secretory effect by inhibition of the gastrointestinal H+K+ATPase enzyme (Fellenius, E., Berglindh, T., Sachs, G., Olke, L., Elander, B., Sjostrand, S. E., and Wallmark, B., 1981, Nature, 290, 159-61).

In a further aspect therefore the present invention provides compounds of structure (I) and pharmaceutically acceptable salts thereof for use in therapy. The compounds of structure (I) and their pharmaceutically acceptable salts inhibit exogenously and endogenously stimulated gastric acid secretion and are useful in the treatment of gastrointestinal diseases in mammals, in particular humans.

Such diseases include, for example, gastric and duodenal ulcers, aspiration pneumonitis and Zollinger-Ellison Syndrome.

Further, the compounds of structure (I) can be used in the treatment of other disorders where an anti-secretory effect is desirable for example in patients with gastritis, NSAID induced gastritis, acute upper intestinal bleeding, in patients with a history of chronic and excessive alcohol consumption, and in patients with gastro oesophageal reflux disease (GERD).

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier or diluent.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) or diluents for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) or diluents routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of structure (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the structure (I) or a pharmaceutically acceptable salt thereof calculated as the free base.

The present invention also provides a method of inhibiting gastric acid secretion which comprises administering to a mammal in need thereof an effective amount of a compound of the structure (I) or a pharmaceutically acceptable salt thereof; and a method of treatment of diseases of the stomach or intestine based on increased acid secretion which comprises administering to a mammal in need thereof an effective amount of a compound of structure (I) or a pharmaceutically acceptable salt thereof.

The pharmaceutically acceptable compounds of the invention will normally be administered to a subject for the treatment of gastro-intestinal diseases and other conditions caused or exacerbated by gastric acidity. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of structure (I) or a pharmaceutically acceptable salt thereof calculated as the free base, the compound being administered 1 to 4 times per day.

Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-flammatory drugs (for example indomethacin, aspirin or naproxen), steroids, or nitrite scavengers (for example astorbit acid or aminosulphonic acid), or other drugs used for treating gastric ulcers (for example pirenzipine, prostanoids for example 16,16 dimethyl PGE2, or histamine $H_2$-antagonists (for example, cimetidine).

The following examples illustrate the invention. Temperatures are recorded in degrees centigrade.

EXAMPLE 1

Preparation of 3-butyryl-4-(2-methylphenylamino)-8-(hydroxymethyl)quinoline

A. Preparation of ethyl 2-butyryl-3-(2-(hydroxymethyl)phenylamino)acrylate.

A mixture of ethyl 2-butyryl-3-ethoxyacrylate (23.5 g, 0.11 mol) and 2-aminobenzyl alcohol (12.3 g, 0.1 mol) was heated to 100° for 10 minutes, then diluted with petroleum ether. On cooling, ethyl 2-butyryl-3-(2-(hydroxymethyl)phenylamino)acrylate (24.9 g, 85%) crystallised as a mixture of E/Z isomers, and was filtered off and washed with petroleum ether.

B. Preparation of ethyl 2-butyryl-3-(2-(4-methoxybenzoyl-oxymethyl)phenylamino)acrylate Ethyl 2-butyryl-3-(2-(hydroxymethyl)phenylamino)-acrylate (14.6 g, 50 mmol) was dissolved in pyridine (50 ml), cooled in ice, and p-anisoyl chloride (12.8 g, 75 mmol) added dropwise. The mixture was stirred 16 hours with warming to room temperature, then evaporated, taken up in dichloromethane, washed with aqueous sodium bicarbonate, dried and evaporated. Crystallisation from ether gave ethyl 2-butyryl-3-(2-(4-methoxybenzoyloxymethyl)phenylamino)acrylate (12.3 g, 58%).

C. Preparation of 3-butyryl-8-(4-methoxybenzoyloxymethyl)-4(1H)-quinolone

Ethyl 2-butyryl-3-(2-(4-methoxybenzoyloxymethyl)-phenylamino)acrylate (12.2 g, 28.7 mmol) was added in portions to boiling diphenyl ether (200 ml), then heated at reflux for 30 minutes. Most of the diphenyl ether was distilled off in vacuo, and the residue triturated with ether to give 3-butyryl-8-(4-methoxybenzoyloxymethyl)-4(1H)-quinolone (5.85 g, 54%), m.p. 156°–162°.

D. Preparation of 3-butyryl-4-chloro-8-(4-methoxybenzoyloxymethyl)quinoline

A solution of 3-butyryl-8-(4-methoxybenzoyloxymethyl)-4(1H)-quinolone (5.75 g, 15.1 mmol) in phosphoryl chloride (75 ml) was heated at reflux for 30 minutes, the phosphoryl chloride evaporated in vacuo, the residue poured onto ice, neutralised with sodium bicarbonate, and extracted into dichloromethane. Drying, evaporation, and trituration with ether gave the crude 3-butyryl-4-chloro-8-(4-methoxy-benzoyloxymethyl)quinoline, which was used without further purification.

E. Preparation of 3-butyryl-4-(2-methylphenylamino-8-(4-methoxybenzoyloxymethyl)quinoline A solution of 3-butyryl-4-chloro-8-(4-methoxybenzoyloxymethyl)quinoline (3.3 g, 8.3 mmol) and 2-methylaniline (1.33 ml, 12.4 mmol) in 1,4-dioxan (30 ml) was heated at reflux for 2 hours, then the dioxan evaporated and the product converted to free base. Recrystallisation from ethanol gave 3-butyryl-4-(2-methylphenylamino-8-(4-methoxybenzoyloxymethyl)quinoline (3.5 g, 90%), m.p. 135°-137°.

F. Preparation of 3-butyryl-4-(2-methylphenylamino)-8-(hydroxymethyl)quinoline

A solution of 3-butyryl-4-(2-methylphenylamino-8-(4-methoxybenzoyloxymethyl)quinoline (3.44 g, 7.3 mmol) and potassium hydroxide (0.56 g, 10 mmol) in ethanol (100 ml) was heated at reflux for 30 minutes, then the solvent evaporated, water added, and the product extracted into dichloromethane. Chromatography (silica gel, 1-2% methanol in dichloromethane) and recrystallisation from methanol gave 3-butyryl-4-(2-methylphenylamino)-8-(hydroxymethyl)quinoline (0.48 g, 20%), m.p. 148°-150°.

$C_{21}H_{22}N_2O_2$ Found C 75.40, H 6.73, N 8.42 Requires C 75.42, H 6.63, N 8.38

EXAMPLE 2

Preparation of 3-butyryl-4-(2-methylphenylamino)-8-(2-methoxyethoxy)quinoline

A. Preparation of 3-butyryl-4-chloro-8-hydroxyquinoline

3-Butyryl-4-chloro-8-methoxyquinoline (26.3 g, 0.1 mol) in dichloromethane (250 ml) was cooled to −78° under nitrogen, and boron tribromide (75 g, 0.3 mol) added slowly. The solution was stirred overnight, warming gradually to room temperature, then quenched with water. The organic solution was separated and evaporated to give the crude product, which was used immediately without further purification.

B. Preparation of 3-butyryl-4-(2-methylphenylamino)-8-hydroxyquinoline

The product of the previous step was dissolved in dioxan (250 ml), 2-methylaniline (10.7 ml, 0.15 mol) added, and the solution refluxed for 1 hour. The solvent was evaporated, the residue taken up in dichloromethane, washed with aqueous sodium hydrogen carbonate, dried and evaporated. Recrystallisation from methanol gave 3-butyryl-4-(2-methylphenylamino)-8-hydroxyquinoline (20.9 g), m.p. 113°-115°.

C. Preparation of 3-butyryl-4-(2-methylphenylamino)-8-(2-methoxyethoxy)quinoline A solution of 3-butyryl-4-(2-methylphenylamino)-8-hydroxyquinoline (3.20 g, 10 mmol) and potassium t-butoxide (1.47 g, 12 mmol) in dry tetrahydrofuran (100 ml) was heated at reflux for 5 minutes, then 2-methoxyethyl benzenesulphonate (4.33 g, 20 mmol) added and hearing continued for 18 hours. Evaporation of the solvent, chromatography (silica gel, 1-2% methanol in dichloromethane) and recrystallisation from ethyl acetate gave 3-butyryl-4-(2-methylphenylamino)-8-(2-methoxy-ethoxy)quinoline (1.42 g, 38%), m.p. 75°-77°.

$C_{23}H_{26}N_2O_3.0.1H_2O$ Found C 72.55, H 6.82, N 7.33 Requires C 72.64, H 6.94, N 7.37

EXAMPLE 3

Preparation of 3-butyryl-4-(4-hydroxy-2-methylphenylamino)-8-(hydroxymethyl)quinoline hydrochloride A. Preparation of 3-butyryl-4-(4-hydroxy-2-methylphenylamino)-8-(4-methoxybenzoyloxymethyl)quinoline A solution of 3-butyryl-4-chloro-8-(4-methoxybenzoyloxymethyl)quinoline (2.56 g, 6.4 mmol) and 4-amino-3-methylphenol (1.18 g, 9.6 mmol) in 1,4-dioxan (30 ml) was heated at reflux for 2 hours, then evaporated. Chromatography (silica gel, 1% methanol in dichloromethane) and recrystallisation from ethanol gave 3-butyryl-4-(4-hydroxy-2-methylphenylamino)-8-(4-methoxybenzoyloxymethyl)-quinoline, (2.36 g, 76%), m.p. 171°-175°.

B. Preparation of 3-butyryl-4-(4-hydroxy-2-methylphenyl-amino)-8-(hydroxymethyl)quinoline hydrochloride A solution of 3-butyryl-4-(4-hydroxy-2-methylphenylamino)-8-(4-methoxybenzoyloxymethyl)quinoline (2.34 g, 4.8 mmol) and sodium hydroxide (0.38 g, 9.6 mmol) in methanol (50 ml) was heated at reflux for 30 minutes, then diluted with water and neutralised with dilute hydrochloric acid. The solid was filtered off and washed with water, then converted to the hydrochloride. Recrystallisation from aqueous ethanol gave 3-butyryl-4-(4-hydroxy-2-methylphenylamino)-8-(hydroxymethyl)quinoline hydrochloride (1.16 g, 62%), m.p. 167°-171°.

$C_{21}H_{22}N_2O_3.HCl.0.5H_2O$ Found C 63.60, H 5.86, N 7.00, Cl 18.69 Requires C 63.71, H 6.11, N 7.08, Cl 18.95

EXAMPLE 4

Preparation of 3-butyryl-4-(2-methylphenylamino)-8-(1-hydroxyethyl)quinoline

A. Preparation of 3-butyryl-4-(2-methylphenylamino)quinoline-8-carbaldehyde

Oxalyl chloride (18.22 g, 0.144 mol) in dichloromethane (180 ml, dried over molecular sieves) was cooled to −70° C., and a solution of dimethylsulphoxide (13.08 g, 0.168 mol) in dry dichloromethane (20 ml) added dropwise under nitrogen with stirring, keeping the temperature below −60° C. After 30 minutes, a solution of 3-butyryl-4-(2-methylphenylamino)-8-hydroxymethylquinoline (40 g, 0.12 mol) in dry dichloromethane (700 ml) was added dropwise below −60° C. After a further 30 minutes, triethylamine (102 ml) was added dropwise, and the mixture allowed to warm to room temperature, washed with water and dried (Na2SO4). The filtered solution was evaporated to a yellow oil, which crystallised on trituration with ether to give the title compound (33.02 g), m.p. 142°-4°.

B. Preparation of 3-butyryl-4-(2-methylphenylamino)-8-(1-hydroxyethyl)quinoline

A solution of 3-butyryl-4-(2-methylphenylamino)-quinoline-8-carbaldehyde (2.0 g, 6 mmol) in dichloromethane (100 ml) was stirred at 0°-5° C. and treated with a solution of methylmagnesium iodide in ether until T.L.C. (2% methanol in dichloromethane) showed that mostly new product had formed. The mixture was washed with ammonium chloride solution, dried and evaporated. Chromatography (silica gel, 0.5% methanol in dichloromethane) afforded the required 3-butyryl-4-(2-methylphenylamino)-8-(1-hydroxyethyl)quinoline (0.28 g) as yellow crystals, m.p. 140°-2° C.

$C_{22}H_{24}N_2O_2$ Found C 75.81, H 7.04, N 8.01 Requires C 75.83, H 6.94, N 8.04

EXAMPLE 5

Preparation of 3-butyryl-4-(2-methylphenylamino)-6-(hydroxymethyl)quinoline

A. Preparation of ethyl 2-butyryl-3-(4-hydroxymethylphenylamino)acrylate

4-Aminobenzylalcohol (25 g) and ethyl 2-butyryl-3-ethoxyacrylate (61 g) were heated together on a rotary evaporator (bath temp 100°) for 30 minutes. Ethyl 2-butyryl-3-(4-(hydroxymethyl)phenylamino)acrylate (49.5 g, 84%) crystallized on standing, was filtered off, washed with a little petroleum ether and vacuum dried, m.p. 44°–6°

B. Preparation of ethyl 2-butyryl-3-(4-benzoyloxymethylphenylamino)acrylate

A solution of ethyl 2-butyryl-3-(4-hydroxymethylphenylamino)acrylate (49.5 g, 0.17 mol) and pyridine (50 ml) in chloroform (250 ml) was stirred at 0°–5° (ice-bath). Benzoyl chloride (22 ml, 0.19 mol) in chloroform (250 ml) was added dropwise keeping the reaction temperature below 10° C. Cooling was removed and the mixture was stirred overnight at room temperature. The mixture was washed with 2M HCl, sodium hydrogen carbonate solution and brine, dried (anhyd. MgSO4), filtered and evaporated to an oil which crystallized on standing. The product was slurried with petroleum ether, filtered off and washed with petroleum ether to give ethyl 2-butyryl-3-(4-benzoyloxymethylphenylamino)acrylate as white crystals (61.8 g, 92%), m.p. 73°–5° C.

C. Preparation of 3-butyryl-6-(benzoyloxymethyl)-4(1H)-quinolone

Ethyl-2-butyryl-3-(4-benzoyloxymethylphenylamino)acrylate (50 g) was added portionwise to boiling diphenyl ether (500 ml) and hearing continued under reflux for 30 minutes. On cooling, crystals started to appear and the mixture was diluted with petroleum ether to give 3-butyryl-6-(benzoyloxymethyl)-4(1H)-quinolone (39.7 g, 96%) as light brown crystals, m.p. 220°–3° C.

D. Preparation of 3-butyryl-4-chloro-6-(benzoyloxymethyl)-quinoline

3-Butyryl-6-(benzoyloxymethyl)-4(1H)-quinolone (30 g) was heated under reflux in phosphorus oxychloride (200 ml) for 30 minutes. The solvent was evaporated and the residue partitioned between dichloromethane and ammonia solution. The organic layer was washed successively with sodium hydrogen carbonate solution and 50% brine. Dried (anhyd. MgSO4), filtered and evaporated to an oily solid which crystallized on trituration with petroleum ether to give 3-butyryl-4-chloro-6-(benzoyloxymethyl)quinoline (21.2 g, 67%), m.p. 85°–6° C.

E. Preparation of 3-butyryl-4-(2-methylphenylamino)-6-benzoyloxymethylquinoline

3-Butyryl-4-chloro-6-benzoyloxymethylquinoline (10 g, 30 mmol) and o-toluidine (3.7 ml, 35 mmol) were heated together under reflux in 1,4-dioxan (150 ml) for 1.5 hours.

The solvent was evaporated and the residue dissolved in chloroform, washed with 2M HCl, sodium hydrogen carbonate solution (×2) and brine, dried, filtered and evaporated to an oil which immediately crystallized to give 3-butyryl-4-(2-methylphenylamino)-6-benzoyloxymethyl quinoline (8.6 g, 66%), m.p. 142°–4° C.

F. Preparation of 3-butyryl-4-(2-methylphenylamino)-6-hydroxymethylquinoline

3-Butyryl-4-(2-methylphenylamino)-6-benzoyloxymethyl-quinoline (3.0 g, 6.8 mmol) was dissolved in methanol (50 ml) and 2M sodium hydroxide solution (50 ml) was added. The mixture was heated under reflux for 45 minutes until a clear solution was obtained. The mixture was partitioned between chloroform and water, the aqueous layer re-extracted with chloroform and the combined organic solutions washed with brine, dried, filtered and evaporated. Crystallisation from ether afforded 3-butyryl-4-(2-methylphenylamino)-6-hydroxymethylquinoline; (1.9 g, 83%), m.p. 139°–41° C.

$C_{21}H_{22}N_2O_2$ Found C 75.32, H 6.52, N 8.37

Requires C 75.42, H 6.63, N 8.36

EXAMPLE 6

Preparation of 3-butyryl-4-(2-methylphenylamino)-7-(hydroxymethyl)quinoline

A. Preparation of ethyl-2-butyryl-3-(3-hydroxymethylphenylamino)acrylate

3-Aminobenzyl alcohol (24.63 g, 0.2 mol) and ethyl butyrylacetate (53.56 g, 0.2 mol) were heated at 150° for 2 hours, then cooled, diluted with petroleum ether (b.p. 60°–80°) and allowed to crystallise at 0° C. Filtration and washing gave the title compound (58.27 g) as a mixture of Z and E isomers.

B. Preparation of ethyl-2-butyryl-3-(3-benzoyloxymethyl-phenylamino)acrylate

To a stirred and cooled (ice-bath) solution of ethyl-2-butyryl-3-(3-hydroxymethylphenylamino)acrylate (29.13 g, 0.1 mol) in pyridine was added dropwise benzoyl chloride (21.09 g, 0.15 mol). The ice bath was removed and the mixture stood for 16 hours, then evaporated, treated with chloroform (200 ml) and washed with saturated aqueous sodium bicarbonate (200 ml), water (200 ml), and 2N hydrochloric acid (2×150 ml). After drying (Na2SO4) and stirring with charcoal, the solution was filtered and evaporated to an oil, which crystallised slowly under petroleum ether (b.p. 40–60) to give the title compound (34.5 g) m.p. 59°–63°.

C. Preparation of 3-butyryl-7-benzoyloxymethyl-4-(1H)-quinolone

Ethyl-2-butyryl-3-(3-benzoyloxymethyl-phenylamino)-acrylate (34.37 g, 86.9 mmol) was added portionwise to refluxing diphenyl ether (300 ml) then heated at reflux for 1 hour. After cooling, petroleum ether (b.p. 40°–60°) was added, and the precipitated solid filtered off. Purification by column chromatography (silica, methanol-chloroform) gave the title compound as a solid (10.52 g) m.p. 228°–31°, from dichloromethane.

D. Preparation of 3-butyryl-4-chloro-7-benzoyloxymethyl-quinoline

3-Butyryl-7-benzoyloxymethyl-4(1H)-quinolone (10.42 g, 29.8 mmol) and phosphoryl chloride (60 ml) were refluxed for 1 hour, then evaporated, and the residue poured onto ice (300 g) with stirring. After neutralising with concentrated ammonia, the product was extracted into chloroform and the solution dried (Na2SO4) and evaporated to a solid. Trituration with ether gave the title compound (9.76 g), m.p. 66°–8°.

E. Preparation of 3-butyryl-4-(2-methylphenylamino)-7-benzoyloxymethylquinoline

3-Butyryl-4-chloro-7-benzoyloxymethylquinoline (3.68 g, 10 mmol) and o-toluidine (1.61 g, 15 mmol) in dioxan (100 ml) were refluxed for 2.5 hours, then allowed to cool and stand for 16 hours. The solvent was evaporated and the product converted to the free base and recrystallised from ethanol to give the title compound (1.8 g), m.p. 110°–12°.

F. Preparation of 3-butyryl-4-(2-methylphenylamino)-7-hydroxymethylquinoline

To a stirring suspension of 3-butyryl-4-(2-methylphenylamino)-7-benzoylmethylquinoline (2.74 g, 6.25 mmol) in methanol (25 ml) was added 2N sodium hydroxide (6.24 ml). Stirring was continued for 18 hours, then the solvent evaporated in vacuo and the residue treated with water and extracted with chloroform. The combined extracts were dried (Na2SO4) and evaporated to a solid, which was purified by column chromatography (silica, chloroform-methanol) to give the title compound (1.31 g), m.p. 176°–8°, from methanol.

$C_{22}H_{22}N_2O_3$ Found C 75.17, H 6.56, N 8.31 Requires C 75.42, H 6.63, N 8.38

EXAMPLE 7

Preparation of 3-isobutyryl-4-(2-methylphenylamino)-8-(hydroxymethyl)quinoline

A. Preparation of ethyl 2-isobutyryl-3-ethoxyacrylate

A mixture of ethyl isobutyrylacetate (60.5 g, 0.38 mol), triethyl orthoformate (126 ml, 0.76 mol) and acetic anhydride (36 ml, 0.38 mol) was heated at reflux for 24 hours, then the volatile components removed in vacuo, finally at 100°/0.5 mm. The residue consisted mainly of ethyl 2-isobutyryl-3-ethoxyacrylate as a mixture of E/Z isomers, and was used without further purification.

B. Preparation of ethyl 2-isobutyryl-3-(2-(hydroxymethyl)phenylamino)acrylate.

2-Aminobenzyl alcohol (12.32 g, 0.1 mol) was dissolved in ethyl 2-isobutyryl-3-ethoxyacrylate (23.57 g, 0.11 mol), stirred for 2 hours at room temperature then warmed briefly to boiling. Cooling and trituration with petroleum ether gave ethyl 2-isobutyryl-3-(2-(hydroxymethyl)phenylamino)acrylate (22.29 g, 77%) as a mixture of E/Z isomers, m.p. 72°–84°.

C. Preparation of ethyl 2-isobutyryl-3-(2-(benzoyloxymethyl)phenylamino)acrylate.

Ethyl 2-isobutyryl-3-(2-(hydroxymethyl)phenylamino)acrylate (22.14 g, 76 mmol) was dissolved in pyridine (150 ml), cooled in ice, benzoyl chloride (13.9 ml, 120 mmol) added, and the mixture stirred overnight. The pyridine was evaporated, aqueous sodium bicarbonate added, the product extracted into dichloromethane, dried, evaporated and crystallised from methanol to give ethyl 2-isobutyryl-3-(2-(benzoyloxymethyl)phenylaminoacrylate (29.40 g, 98%), m.p. 76°–84°.

D. Preparation of 3-isobutyryl-8-(benzoyloxymethyl)-4(1H)quinolone.

Diphenyl ether (500 ml) was heated to reflux, ethyl 2-isobutyryl-3-(2-(benzoyloxymethyl)phenylaminoacrylate (29.3 g, 74.1 mmol) added, and heating continued for 15 minutes. The bulk of the diphenyl ether was removed by vacuum distillation, and the residue chromatographed (silica gel, 1–2.5% methanol in dichloromethane) and recrystallised from ethyl acetate to give 3-isobutyryl-8-(benzoyloxymethyl)-4(1H)-quinolone (11.9 g, 46%), m.p. 158°–160°.

E. Preparation of 3-isobutyryl-4-chloro-8-(benzoyloxymethyl)quinoline.

A solution of 3-isobutyryl-8-(benzoyloxymethyl)-4(1H)-quinolone (11.81 g, 29.9 mmol) in phosphoryl chloride (100 ml) was heated at reflux for 2.5 hours, then the excess phosphoryl chloride evaporated. Water was added and the product extracted into a mixture of dichloromethane and isopropyl alcohol. Drying and evaporation of the organic layer gave crude 3-isobutyryl-4-chloro-8-(benzoyloxymethyl)quinoline (12.0 g), contaminated with isopropyl alcohol. This was used without further purification.

F. Preparation of 3-isobutyryl-4-(2-methylphenylamino)-8-(hydroxymethyl)quinoline.

A solution of 3-isobutyryl-4-chloro-8-(benzoyloxymethyl)quinoline (3.68 g, 10 mmol) and 2-methylaniline (2.13 ml, 20 mmol) in dioxan (50 ml) was heated at reflux for 2 hours, then evaporated, taken up in dichloromethane, washed with aqueous sodium bicarbonate, water and brine, dried and evaporated to an oil. This was taken up in 1% methanolic sodium hydroxide solution (100 ml) and stirred vigorously for 1 hour. The methanol was evaporated, water and dichloromethane added, the aqueous phase adjusted to pH 10 and extracted with dichloromethane. The organic extracts were dried, evaporated and chromatographed (silica gel, 1–2% methanol in dichloromethane).

Trituration of the product fractions with ether followed by recrystallisation from aqueous methanol gave 3-isobutyryl-4-(2-methylphenylamino)-8-(hydroxymethyl)quinoline (1.46 g, 44%), m.p. 116°–118°.

$C_{21}H_{22}N_2O_2$ Found C 75.31, H 6.53, N 8.40 Requires C 75.42, H 6.63, N 8.38

EXAMPLE 8

Preparation of 3-isobutyryl-4-(4-fluoro-2-methylphenylamino)-8-(hydroxymethyl)quinoline A solution of 3-isobutyryl-4-chloro-8-(benzoyloxymethyl)quinoline (1.84 g, 5 mmol) and 4-fluoro-2-methylaniline (0.78 ml, 7 mmol) in dioxan (25 ml) was heated at reflux for 2 hours, then the solvent evaporated. A solution of sodium hydroxide (0.8 g, 20 mmol) in methanol (50 ml) was added and the mixture stirred at room temperature for 1.5 hours. The resulting precipitate was filtered off and recrystallised from methanol to give (0.48 g, 27%), m.p. 139°–140°.

$C_{21}H_{20}FN_2O_2$ Found C 71.24, H 5.99, N 7.84 Requires C 71.57, H 6.01, N 7.95

EXAMPLE 9

Preparation of 3-butyryl-4-(4-fluoro-2-methylphenylamino)-8-(hydroxymethyl)quinoline A. Preparation of ethyl 2-butyryl-3-(2-(benzoyloxymethyl)phenylamino)acrylate.

A solution of ethyl 2-butyryl-3-(2-(hydroxymethyl)phenylaminoacrylate (51.1 g, 0.175 mol) in pyridine (400 ml) was cooled in ice, benzoyl chloride (29 ml, 0.25 mol) added, and the mixture stirred 2 days at room temperature.

The pyridine was evaporated, aqueous sodium bicarbonate added, extracted with dichloromethane, and the organic layers dried and evaporated. Trituration with petroleum ether and washing with cold methanol gave ethyl 2-butyryl-3-(2-(benzoyloxymethyl)phenylamino)acrylate (60.8 g, 88%), m.p. 78°–82°.

B. Preparation of 3-butyryl-8-(benzoyloxymethyl)-4(1H)-quinolone.

Diphenyl ether (500 ml) was heated to boiling, ethyl 2-butyryl-3-(2-(benzoyloxymethyl)phenylamino)acrylate (60.5 g, 0.15 mol) added, and heating continued at reflux for 25 minutes. Most of the diphenyl ether was removed by vacuum distillation. Chromatography (silica gel, 0–3% methanol in dichloromethane) and recrystallisation from methanol gave 3-butyryl-8-(benzoyloxymethyl)-4(1H)-quinolone (24.1 g, 45%), m.p. 115°–11°.

C. Preparation of 3-butyryl-4-chloro-8-(benzoyloxymethyl)quinoline.

A solution of 3-butyryl-8-(benzoyloxymethyl)-4(1H)-quinolone (17.93 g) in phosphoryl chloride (150 ml) was heated at reflux for 1.5 hours, then the excess phosphoryl chloride evaporated. The residue was poured onto ice, extracted with dichloromethane, dried and evaporated to give 3-butyryl-4-chloro-8-(benzoyloxymethyl)quinoline. The crude product was used without further purification.

D. Preparation of 3-butyryl-4-(2-methyl-4-fluorophenyl-amino)-8-(hydroxymethyl)quinoline.

A solution of 3-butyryl-4-chloro-8-(benzoyloxymethyl)quinoline (3.68 g, 10 mmol) and 4-fluoro-2-methylaniline (1.67 ml, 15 mmol) in dioxan (40 ml) was heated at reflux for 3 hours, cooled, filtered and the solid discarded. The solution was evaporated and the residue taken up in 1% methanolic sodium hydroxide (100 ml) and stirred 2 hours at room temperature. The solid was filtered off and recrystallised from methanol to give 3-butyryl-4-(2-methyl-4-fluorophenylamino)-8-(hydroxymethyl)quinoline (1.56 g, 44%), m.p. 168°–170°.

$C_{21}H_{21}FN_2O_2$ Found C 71.40, H 5.78, N 7.80 Requires C 71.57, H 6.01, N 7.95

EXAMPLE 10

Preparation of 3-butyryl-4-(2-methylphenylamino)-8-(2-hydroxyethoxy)quinoline

3-Butyryl-4-(2-methylphenylamino)-8-hydroxyquinoline (3.2 g, 10 mmol) was dissolved in tetrahydrofuran (150 ml), potassium t-butoxide (1.83 g, 15 mmol) added, stirred to dissolve, then 2-chloroethanol (1.3 ml, 20 mmol) added and the mixture heated at reflux overnight. A further portion of potassium t-butoxide (1.83 g) and of 2-chloroethanol (1.3 ml) was added and heating continued for 2 days. The tetrahydrofuran was evaporated, the residue taken up in dichloromethane, washed with water and brine, dried and evaporated. Recrystallisation from ethyl acetate/petroleum ether gave 3-butyryl-4-(2-methylphenylamino)-8-(2-hydroxyethoxy)quinoline (1.18 g, 32%), m.p. 125°–127°.

$C_{22}H_{24}N_2O_3$ Found C 72.23, H 6.61, N 7.52 Requires C 72.50, H 6.64, N 7.69

EXAMPLE 11

Preparation of 3-butyryl-4-(2-methylphenylamino)-8-(2-(2-hydroxyethoxy)ethoxy)quinoline 3-butyryl-4-(2-methylphenylamino)-8-hydroxyquinoline (2.40 g, 7.5 mmol) and potassium t-butoxide (1.22 g, 10 mmol) were dissolved in tetrahydrofuran (40 ml), 2-(2-chloroethoxy)ethanol (1.58 ml, 15 mmol) added, and the mixture heated at reflux for 18 hours. The solvent was evaporated, the residue taken up in dichloromethane, washed with water and brine, dried and evaporated. Chromatography (silica gel, 3–5% methanol in dichloromethane) and recrystallisation from ethyl acetate gave 3-butyryl-4-(2-methylphenylamino)-8-(2-(2-hydroxyethoxy)ethoxy)quinoline (1.77 g, 60%), m.p. 144°–146°.

$C_{24}H_{28}N_2O_4$ Found C 70.51, H 6.72, N 6.72 Requires C 70.57, H 6.91, N 6.86

EXAMPLE 12

Preparation of 3-butyryl-4-(2-methylphenylamino)-8-(2-(2-(2-hydroxyethoxy)ethoxy)ethoxy)quinoline A mixture of 3-butyryl-4-(2-methylphenylamino)-8-hydroxyquinoline (2.40 g, 7.5 mmol), potassium t-butoxide (1.22 g, 10 mmol) and 2-(2-(2-(chloroethoxy)ethoxy)ethanol (2.18 ml, 15 mmol) in tetrahydrofuran (40 ml) was heated at reflux for 3 days. The solvent was evaporated, the residue taken up in dichloromethane, washed with water and brine, dried and evaporated. Chromatography (silica gel, 0–10% methanol in ethyl acetate) and crystallisation from ether gave 3-butyryl-4-(2-methylphenylamino)-8-(2-(2-(2-hydroxyethoxy)ethoxy)ethoxy)quinoline (2.32 g, 68%) as a hygroscopic solid, m.p. 102°–104°.

$C_{26}H_{32}N_2O_5.0.1H_2O$ Found C 68.61, H 7.17, N 6.04 Requires C 68.73, H 7.14, N 6.17

EXAMPLE 13

Preparation of 3-butyryl-4-(4-fluoro-2-methylphenylamino)-8-(2-(2-hydroxyethoxy)ethoxy)quinoline A. Preparation of 3-butyryl-4-(4-fluoro-2-methylphenyl-amino)-8-hydroxyquinoline A solution of 3-butyryl-4-chloro-8-methoxyquinoline (131.9 g, 0.5 mol) in dichloromethane (1 liter) was cooled to −78°, then boron tribromide (142 ml, 1.5 mol) added slowly over 10 minutes. The mixture was warmed slowly to 0°, stirred 2 hours, then allowed to warm to room temperature overnight. After recooling in ice the reaction was quenched cautiously with water, then the resulting solid filtered off and dried. This was heavily contaminated with boron-containing impurities, but was used without purification. Crude 3-butyryl-4-chloro-8-hydroxyquinoline (64 g) and 4-fluoro-2-methylaniline (16.7 ml, 0.15 mol) were dissolved in dioxan (300 ml), heated on a steam bath for 2 hours, then left to stand overnight. The dioxan was evaporated, dichloromethane and aqueous sodium bicarbonate added, the mixture stirred until all the solid had dissolved, then the organic layer dried and evaporated. Recrystallisation from methanol gave 3-butyryl-4-(4-fluoro-2-methylphenylamino)-8-hydroxy-quinoline (37 g), m.p. 121°–122°.

B. Preparation of 3-butyryl-4-(4-fluoro-2-methylphenyl-amino)-8-(2-(2-hydroxyethoxy)ethoxy)quinoline A solution of 3-butyryl-4-(4-fluoro-2-methylphenylamino)-8-hydroxyquinoline (3.2 g, 10 mmol) and potassium t-butoxide (1.83 g, 15 mmol) in tetrahydrofuran (70 ml) was heated to reflux, 2-chloroethoxyethanol (2.11 ml, 20 mmol) added, and heating continued for 17 hours. The solvent was evaporated, the residue taken up in dichloro-methane, washed with water and brine, dried and evaporated.

Chromatography (silica gel, 3–6% methanol in dichloromethane), after the elution of large amounts of unchanged starting material, gave product fractions which were recrystallised from methanol to give 3-butyryl-4-(4-fluoro-2-methylphenylamino)-8-(2-(2-hydroxyethoxy)ethoxy)-quinoline (0.38 g, 9%), m.p. 144°–145°.

$C_{24}H_{27}FN_2O_4$ Found C 67.68, H 6.43, N 6.59 Requires C 67.59, H 6.38, N 6.57

EXAMPLE 14

Preparation of 3-butyryl-4-(4-fluoro-2-methylphenylamino)-8-(2-hydroxyethoxy)quinoline A solution of 3-butyryl-4-(4-fluoro-2-methylphenylamino)-8-hydroxyquinoline (3.2 g, 9.4 mmol) and potassium t-butoxide (1.83 g, 15 mmol) in tetrahydrofuran (75 ml) was warmed to reflux, 2-chloroethanol (1.3 ml, 20 mmol) added, and heating continued for 2 days. The solvent was evaporated, the residue taken up in dichloromethane, washed with water and brine, dried and evaporated. Chromatography (silica gel, 5% methanol in dichloromethane) gave initially recovered starting material, followed by product fractions which were recrystallised from ethyl acetate/petroleum ether, then from methanol to give 3-butyryl-4-(4-fluoro-2-methylphenylamino)-8-(2-hydroxyethoxy)quinoline as a hygroscopic solid (0.82 g, 23%), m.p. 130°–133°.

$C_{22}H_{23}FN_2O_3.0.8H_2O$ Found C 66.69, H 6.20, N 7.07 Requires C 66.58, H 6.25, N 7.06

EXAMPLE 15

Preparation of 3-butyryl-4-(4-hydroxy-2-methylphenylamino)-8-(1-hydroxyethyl)quinoline A. Preparation of 2-(1-hydroxyethyl)aniline Sodium borohydride (40 g, 1.0 mol) was added portionwise to a stirred solution of o-aminoacetophenone (80 g) in methanol (800 ml) at 0°, allowing the effervescence to subside between each addition. Cooling was removed and the mixture allowed to warm to reflux temperature to complete the reaction. When cool, the solvent was evaporated and the residue partioned between dichloromethane-water. The organic solution was washed successively with water and brine, dried (anhyd. MgSO4), filtered and evaporated to a light yellow oil which crystallised from petroleum spirit (40°–60°) to give white crystals (52 g, 64%), m.p. 50°–52°.

B. Preparation of ethyl 2-butyryl-3-(2-(1-hydroxyethyl)phenylamino)acrylate 2-(1-hydroxyethyl)aniline (30 g, 0.32 mol) and ethyl 2-butyryl-3-ethoxyacrylate (47.3 g, 0.22 mol) were heated together on a rotary evaporator (bath temperature 100° C.) for 1 hour to give ethyl 2-butyryl-3-(2-(1-hydroxyethyl)-phenylamino)acrylate as an oil (65 g, 96%).

C. Preparation of ethyl 2-butyryl-3-(2-(1-benzoyloxyethyl)phenylamino)acrylate

A solution of ethyl 2-butyryl-3-(2-(1-hydroxyethyl)-phenylamino)acrylate (63 g, 0.2 mol) and pyridine (50 ml in dichloromethane (400 ml) were stirred at 0° C. and treated with benzoyl chloride (50 ml) in dichloromethane (100 ml) added at such a rate to keep the reaction temperature below 10° C. The cooling bath was removed and the mixture was stirred at ambient temperature for 2 hours. The solution was washed with 2M hydrochloric acid (×2), saturated sodium hydrogen carbonate solution, water and brine, dried (anhyd. MgSO4), filtered and evaporated-to an orange oil (70 g, 83%).

D. Preparation of 3-butyryl-8-vinyl-4(1H)-quinolone

Ethyl 2-butyryl-3-(2-(1-benzoyloxyethyl)-phenylamino)acrylate (70 g, 0.17 mol) was added dropwise to boiling diphenyl ether (700 ml) keeping the reaction temperature above 240° C. The mixture was heated under reflux for 1 hour then cooled rapidly. The mixture was chromatographed (silica gel, dichloromethane+methanol (2–4%)) to afford the required compound as a light solid (23.2 g, 56%) m.p. 206°–8° C.

E. Preparation of 3-butyryl-4-chloro-8-vinylquinoline

3-Butyryl-8-vinylquinolone (23 g, 95 mmol) was heated under reflux in a mixture of phosphoryl chloride (100 ml) and chloroform (100 ml) for 45 minutes. The solvent was evaporated and the residue was mixed with ice, neutralized with ammonia solution and extracted into dichloromethane. The organic solution was washed successively with sodium hydrogen carbonate solution and brine, dried (anhyd. MgSO4), filtered and evaporated. Chromatography (silica gel, 2% methanol in di.chloromethane) afforded 3-butyryl-4-chloro-8-vinylquinoline as a brown oil (9.5 g, 38.5%).

F. Preparation of 3-butyryl-4-(4-hydroxy-2-methylphenylamino)-8-vinylquinoline

3-Butyryl-4-chloro-8-vinylquinoline (20.0 g, 77 mmol) and 4-amino-m-cresol (9.5 g, 77 mmol) were heated together under reflux in 1,4-dioxan (150 ml) for 2.5 hours. The solvent was evaporated and the residue was dissolved in dichloromethane, washed with water, 2M hydrochloric acid, sodium hydrogen carbonate solution and brine. The solution was dried (anhyd. MgSO4), filtered and evaporated to an oil which was chromatographed (silica gel, 1% methanol in dichloromethane) to give 3-butyryl-4-(4-hydroxy-2-methylphenylamino)-8-vinylquinoline as orange crystals (9.0 g, 32%) m.p. 150°–2°.

G. Preparation of 3-butyryl-4-(4-hydroxy-2-methylphenyl-amino)quinoline-8-carbaldehyde 3-Butyryl-4-(4-hydroxy-2-methylphenylamino)-8-vinylquinoline (5.0 g, 14.4 mmol) was stirred at −60° C. in a mixture of methanol (100 ml) and dichloromethane (200 ml) and ozone bubbled through for 15 minutes. The ozone mixture was flushed out of the reaction with nitrogen. Dimethylsulphide (2.5 ml) was added and the mixture allowed to warm to room temperature. The solvent was evaporated and the residue was chromatographed (silica gel, methanol 1% in dichloromethane) to afford 3-butyryl-4-(4-hydroxy-2-methylphenylamino)quinoline-8-carbaldehyde (2.1 g, 42%) as an oil.

H. Preparation of 3-butyryl-4-(4-hydroxy-2-methylphenyl-amino)-8-(1-hydroxyethyl)quinoline 3-Butyryl-4-(4-hydroxy-2-methylphenylamino)-quinoline-8-carbaldehyde (2.0 g, 6 mmol) was stirred in dry tetrahydrofuran (200 ml) at j−30° C. and treated with a solution of methylmagnesium iodide in ether. Cooling was removed and the mixture was allowed to warm to room temperature. The mixture was washed with saturated ammonium chloride solution (×2) and the aqueous extracted with dichloromethane. The combined organics were dried and evaporated to afford a brown oil which was chromatographed (silica gel, 1% methanol in dichloromethane) to return aldehyde starting material (0.16 g ) and give 3-butyryl-4-(4-hydroxy-2-methyl-phenylamino)-8-(1-hydroxyethyl)quinoline as yellow crystals from ether-petrol (0.45 g, 21.5%), m.p. 182°–4° C.

$C_{22}H_{24}N_2O_3.0.15H_2O$ Found C 72.00, H 6.71, N 7.48 Requires C 71.97, H 6.67, N 7.63

EXAMPLE 16

Preparation of 3-isobutyryl-4-(4-hydroxy-2-methylphenylamino)-8-(hydroxymethyl)quinoline hydrochloride A solution of 3-isobutyryl-4-chloro-8-(benzoyloxymethyl)quinoline (3.68 g, 10 mmol) and 4-hydroxy-2-methylaniline (1.35 g, 11 mmol) in dioxan (50 ml) was heated at reflux for 2 hours, then the dioxan evaporated and the residue taken up in 1% methanolic sodium hydroxide (100 ml) and stirred 1.5 hours at room temperature. The methanol was evaporated, the residue taken up in water, adjusted to pH 7, and the solid filtered off. This was converted to the salt with ethanolic hydrogen chloride, then recrystallised from aqueous ethanol to give 3-isobutyryl-4-(2-methylphenylamino)-8-(hydroxymethyl)quinoline hydrochloride (1.15 g, 30%), m.p. 225°–255° (dec).

$C_{21}H_{22}N_2O_3 \cdot HCl$ Found C 65.19, H 5.98, N 7.24, $C_{18.77}$ Requires C 65.19, H 5.99, N 7.24, $C_{19.16}$

EXAMPLE 17

Preparation of 3-butyryl-4-(4-fluoro-2-methylphenylamino)-8-(2-methoxyethoxy)quinoline A solution of 3-butyryl-4-(4-fluoro-2-methylphenylamino)-8-hydroxyquinoline (3.38 g,. 10 mmol) and potassium t-butoxide (1.68 g, 15 mmol) in tetrahydrofuran (75 ml) was warmed to near boiling, chloroethyl methyl ether (1.83 ml, 20 mmol) added, and the mixture heated at reflux for 3 days. The solvent was evaporated then the product taken up in dichloromethane, washed with water and brine, dried and evaporated. Chromatography (silica gel, ethyl acetate/2% acetic acid/0–5% methanol) and recrystallisation from ethyl acetate/petroleum ether gave 3-butyryl-4-(4-fluoro-2-methylphenylamino)-8-(2-methoxyethoxy)quinoline (0.41 g), m.p. 124°–5°.

$C_{23}H_{25}FN_2O_2$ Found C 69.71, H 6.52, N 7.02 Requires C 69.68, H 6.36, N 7.07

EXAMPLE 18

Preparation of 3-isobutyryl-4-(2-methylphenylamino)-8-(2-hydroxyethoxy)quinoline A. Preparation of 3-isobutyryl-4-chloro-8-methoxyquinoline 3-Isobutyryl-8-methoxy-4(1H)-quinolone (39.4 g, 0.16 mol) and phosphoryl chloride (315 ml) were stirred at room temperature for 10 rain, then ether (700 ml) added. After a further 16 hours the yellow precipitate was filtered off, washed with ether, and added to crashed ice with stirring.

The mixture was neutralised with 10% aqueous sodium carbonate and the product extracted into dichloromethane (3×250 ml), dried and evaporated to an oil. Treatment with petroleum ether (60°–80°) gave 3-isobutyryl-4-chloro-8-methoxy-quinoline (34.8 g) as a white crystalline solid, m.p. 90°–92°.

B. Preparation of 3-isobutyryl-4-chloro-8-hydroxyquinoline

A solution of 3-isobutyryl-4-chloro-8-methoxyquinoline (21.1 g, 80 mmol) in dichloromethane (320 ml) was cooled to −10° and boron tribromide (60.13 g, 240 mmol) added dropwise under nitrogen. The solution was allowed to warm to room temperature, and after 16 hours was poured onto crushed ice (500 g). The layers were separated, and the aqueous layer further extracted with dichloromethane. The combined extracts were washed with brine, dried and evaporated to a yellow solid (29.75 g). This complex of 3-isobutyryl-4-chloro-8-hydroxyquinoline was used without further purification.

C. Preparation of 3-isobutyryl-4-(2-methylphenylamino)-8-hydroxyquinoline

The 3-isobutyryl-4-chloro-8-hydroxyquinoline complex (14.88 g) and 2-methylaniline (6.43 g, 60 mmol) in dioxan (250 ml) were heated under reflux for 3 hours. The solvent was evaporated and the residue treated with aqueous sodium bicarbonate solution and extracted into dichloromethane. The combined extracts were dried (Na2SO4) and evaporated to a solid which was boiled with methanol, cooled, filtered, washed with methanol and dried to yield 3-isobutyryl-4-(2-methylphenylamino)-8-hydroxyquinoline (8.72 g), m.P. 131°–133°.

D. Preparation of 3-isobutyryl-4-(2-methylphenylamino)-8-(2-hydroxyethoxy)quinoline To a solution of 3-isobutyryl-4-(2-methylphenylamino)-8-hydroxyquinoline (5 g, 15.6 mmol) in dry tetrahydrofuran (250 ml) was added potassium t-butoxide (2.63 g, 23.4 mmol), followed by 2-bromoethanol (3.9 g, 31.2 mmol). The stirred mixture was heated under reflux for 16 hours, then a further quantity of potassium t-butoxide (2.63 g, 23.4 mmol) and 2-bromoethanol (3.9 g, 31.2 mmol) added, and heating continued for 2 days. The solvent was evaporated, and the residue treated with aqueous sodium bicarbonate and extracted into dichloromethane. The extracts were dried and evaporated to an oil, which was purified by flash chromatography (silica gel, dichloromethane/methanol) and recrystallisation from 40–60 petroleum ether to yield 3-isobutyryl-4-(2-methylphenylamino)-8-(2-hydroxyethoxy)-quinoline (2.25 g), m.p. 154°–156°.

$C_{22}H_{24}N_2O_3 \cdot 0.4\ H_2O \cdot 0.006\ CH_2Cl_2$ Found C 70.55, H 6.61, N 7.31 Requires C 60.33, H 6.67, N 7.44

EXAMPLE 19

Preparation of 3-isobutyryl-4-(4-fluoro-2-methylphenyl-amino)-8-(2-hydroxyethoxy)quinoline A. Preparation of 3-isobutyryl-4-(4-fluoro-2-methylphenylamino)-8-hydroxyquinoline The 3-isobutyryl-4-chloro-8-hydroxyquinoline complex (14.88 g) and 4-fluoro-2-methylaniline (7.53 g, 60 mmol) in dioxan (250 ml) were heated under reflux for 3 hours.

The solvent was evaporated, and the residue treated with aqueous sodium bicarbonate and extracted with dichloromethane. The combined extracts were dried and evaporated to a solid which was boiled with methanol, allowed to cool, filtered off, washed with methanol and dried to yield 3-isobutyryl-4-(2-methylphenylamino)-8-(2-hydroxyethoxy)quinoline (9.07 g), m.p. 138°–140°.

B. Preparation of 3-isobutyryl-4-(4-fluoro-2-methylphenylamino-8-(2-hydroxyethoxy)quinoline To a solution of 3-isobutyryl-4-(4-fluoro-2-methylphenylamino)-8-hydroxyquinoline (5 g, 14.8 mmol) in dry tetrahydrofuran (250 ml) was added potassium t-butoxide (2.49 g, 22.2 mmol), followed by 2-bromoethanol (3.69 g, 29.6 mmol). The stirred mixture was heated under reflux for 16 hours, then a further quantity of potassium t-butoxide (2.49 g, 22.2 mmol) and 2-bromoethanol (3.69 g, 29.6 mmol) added, and heating continued for 2 days. The solvent was evaporated, and the residue treated with aqueous sodium bicarbonate and extracted into dichloromethane. The extracts were dried and evaporated to an oil, which was purified by flash chromatography (silica gel, dichloromethane/methanol) and recrystallisation from ether to yield 3-isobutyryl-4-(4-fluoro-2-methylphenylamino-8-(2-hydroxyethoxy) (1.97 g), m.p. 183°–185°.

$C_{22}H_{23}FN_2O_3 \cdot 0.07H_2O \cdot 0.04Et_2O$ Found C 68.59, H 5.96, N 7.14 Requires C 68.79, H 6.11, N 7.27

EXAMPLE 20

Preparation of 3-isobutyryl-4-(2-methylphenylamino)-8-(2-methoxyethoxy)quinoline A mixture of 3-isobutyryl-4-(2-methylphenylamino)-8-hydroxyquinoline (5.0 g, 15.6 mmol), potassium t-butoxide (2.63 g, 23.4 mmol) and 2-chloroethyl methyl ether (2.85 ml, 31.2 mmol) in tetrahydrofuran (250 ml) was heated at reflux for 3 days, then the solvent evaporated. Water was added, the product extracted into dichloromethane, and the organic extracts dried and evaporated. Chromatography (silica gel, ethyl acetate/2% acetic acid/0–5% methanol) removed unchanged starting material, then further chromatography (silica gel, 1–1.5% methanol in dichloromethane) and crystallisation from petroleum ether (40–60) gave 3-isobutyryl-4-(2-methylphenylamino)-8-(2-methoxyethoxy)quinoline (0.67 g), m.p. 68°–70°.

$C_{23}H_{26}N_2O_3$ Found C 73.10, H 6.97, N 7.23 Requires C 72.99, H 6.92, N 7.40

EXAMPLE 21

Preparation of 3-propanoyl-4-(2-methylphenylamino)-8-(2-hydroxyethoxy)quinoline

A. Preparation of methyl 2-propanoyl-3-methoxyacrylate

A mixture of methyl propionylacetate (112.2 g, 0.86 mol), trimethyl orthoformate (188 ml, 1.72 mol) and acetic anhydride (81 ml, 0.86 mol) was heated at reflux for 17 hours, then the volatile material removed in vacuo, finally at 70°/0.3 mm. The residue was predominantly methyl 2-propanoyl-3-methoxyacrylate, and was used without further purification.

B. Preparation of methyl 2-propanoyl-3-(2-methoxyphenyl-amino)acrylate

A mixture of methyl 2-propanoyl-3-methoxyacrylate (70 g) and 2-methoxyaniline (45 ml) was heated on a steam bath for 30 minutes, then diluted with petroleum ether and left to crystallise. Filtration and washing with ether gave methyl 2-propanoyl-3-(2-methoxyphenylamino)acrylate (78.2 g) as a mixture of E/Z isomers.

C. Preparation of 3-propanoyl-8-methoxy-4(1H)-quinolone

Methyl 2-propanoyl-3-(2-methoxyphenylamino)acrylate (77.7 g, 0.29 mol) was added to boiling diphenyl ether (500 ml) then heated at reflux for 1 hour. The solution was partially cooled and poured into high-boiling petroleum ether, then the solid filtered off and washed with 40–60 petroleum ether to give 3-propanoyl-8-methoxy-4(1H)-quinolone (35.6 g, 52%), m.p. 260°–263°

D. Preparation of 3-propanoyl-4-chloro-8-methoxyquinoline

3-Propanoyl-8-methoxy-4(1H)-quinolone (35.4 g, 0.15 mol) was dissolved in phosphoryl chloride (400 ml) and heated at reflux for 1 hour, then the excess phosphoryl chloride evaporated. The residue was mixed with ice, then diluted with water and extracted into dichloromethane. Drying and evaporation gave 3-propanoyl-4-chloro-8-methoxyquinoline (39.7 g) as a dark oil which was used without further purification.

E. Preparation of 3-propanoyl-4-chloro-8-hydroxyquinoline

3-Propanoyl-4-chloro-8-methoxyquinoline (32 g) was dissolved in dichloromethane (250 ml), cooled to −78°, and boron tribromide (37 ml) added slowly. The solution was allowed to warm slowly to room temperature overnight, then recooled in ice and quenched cautiously with water. The resulting solid was filtered off and washed with water to give crude 3-propanoyl-4-chloro-8-hydroxyquinoline (115 g crude weight), which was used without further purification.

F. Preparation of 3-propanoyl-4-(2-methylphenylamino)-8-hydroxyquinoline

Impure 3-propanoyl-4-chloro-8-hydroxyquinoline (86 g) and 2-methylaniline (10.7 ml) in dioxan (200 ml) were warmed over a steam bath for 30 minutes, then left to stand overnight. After evaporation of the dioxan, dichloromethane and aqueous sodium bicarbonate were added, the organic layer washed with water and brine, dried and evaporated to a yellow solid. Recrystallisation from methanol gave 3-propanoyl-4-(2-methylphenylamino)-8-hydroxyquinoline (11.6 g), m.p. 125°–128°.

G. Preparation of 3-propanoyl-4-(2-methylphenylamino)-8-(2-hydroxyethoxy)quinoline A solution of 3-propanoyl-4-(2-methylphenylamino)-8-hydroxyquinoline (3.06 g, 10 mmol) and potassium t-butoxide (1.68 g, 15 mmol) in diglyme (50 ml) was heated to 150°, a solution of 2-bromoethanol (0.85 ml, 12 mmol) in diglyme (25 ml) added dropwise, then the mixture raised to reflux temperature with vigorous stirring. After 1 hour a further portion of 2-bromoethanol (0.85 ml) was added, and reflux continued for 2 hours. The diglyme was evaporated, the residue taken up in dichloromethane, washed with water and brine, dried and evaporated. Chromatography (silica gel, ethyl acetate/2% acetic acid/2–5% methanol) and recrystallisation from aqueous isobutyl alcohol gave 3-propanoyl-4-(2-methylphenylamino)-8-(2-hydroxyethoxy)quinoline (0.48 g), m.p. 174°–176°.

$C_{21}H_{22}N_2O_3$ Found C 71.92, H 6.20, N 7.88 Requires C 71.98, H 6.33, N 7.99

EXAMPLE 22

Preparation of 3-propanoyl-4-(4-fluoro-2-methylphenyl-amino)-8-(2-hydroxyethoxy)-quinoline A. Preparation of 3-propanoyl-4-(4-fluoro-2-methylphenylamino)-8-hydroxyquinoline Impure 3-propanoyl-4-chloro-8-hydroxyquinoline (28 g) and 2-methylaniline (3.1 ml) in dioxan (100 ml) were warmed over a steam bath for 30 minutes, then left to stand overnight. After evaporation of the dioxan, dichloromethane and aqueous sodium bicarbonate were added, the organic layer washed with water and brine, dried and evaporated to a yellow solid. Recrystallisation from methanol gave 3-propanoyl-4-(4-fluoro-2-methylphenyl-amino)-8-hydroxyquinoline (4.0 g), m.p. 143°–146°.

B. Preparation of 3-propanoyl-4-(4-fluoro-2-methylphenyl-amino)-8-(2-hydroxyethoxy)quinoline A solution of 2-bromoethanol (5.75 ml, 42 mmol) in acetone (25 ml) was added dropwise to a refluxing mixture of 3-propanoyl-4-(4-fluoro-2-methylphenylamino)-8-hydroxyquinoline (1.62 g, 5 mmol), anhydrous potassium carbonate (6.9 g, 50 mmol) and acetone (25 ml) with vigorous stirring. Heating was continued for 18 hours, then water added, the product extracted into dichloromethane, dried and evaporated. Chromatography (silica gel, 2–5% methanol in dichloromethane) and recrystallisation from methanol yielded 3-propanoyl-4-(4-fluoro-2-methylphenylamino)-8-(2-hydroxyethoxy)-quinoline (0.89 g), m.p. 170°–1.72°.

$C_{21}H_{21}FN_2O_3$ Found C 68.32, H 5.90, N 7.37 Requires C 68.46, H 5.75, N 7.60

EXAMPLE 23

Preparation of 3-butyryl-4-(2-methylphenylamino)-8-(2-hydroxyethoxy)quinoline hydrochloride 3-Butyryl-4-(2-methylphenylamino)-8-(2-hydroxyethoxy)quinoline (10 g) was suspended in methanol (100 ml) at room temperature, conc. hydrochloric acid added slowly to give a clear solution, then the solvent evaporated. The residue was twice taken up in 2-propanol and re-evaporated, and was then recrystallised from 2-propanol/ether to obtain the desired salt (9.7 g), m.p. 214°–215° C.

$C_{22}H_{24}N_2O_3.HCl.0.2H_2O$ Found C 65.50, H 6.21, N 6.88 Requires C 65.32, H 6.33, N 6.93.

EXAMPLE 24

Preparation of 3-butyryl-4-(2-methylphenylamino)-8-(2-hydroxyethoxy)quinoline mesylate 3-Butyryl-4-(2-methylphenylamino)-8-(2-hydroxyethoxy)quinoline (60 g) was suspended in ethyl acetate (400 ml), warmed to 50° C., and methanesulphonic acid (16.3 g) added with vigorous stirring. The desired salt crystallised on cooling, and was filtered off and washed with ethyl acetate; yield 50.1 g, m.p. 83°–85° C.

$C_{22}H_{24}N_2O_3.CH_4O_3S.H_2O$ Found C 57.78, H 6.28, N 5.84 Requires C 57.73, H 6.32, N 5.85.

EXAMPLE A

A tablet for oral administration is prepared by combining

|  | Mg/Tablet |
| --- | --- |
| Compound of structure (I) | 100 |
| lactose | 153 |
| Starch | 33 |
| crospovidone | 12 |
| microcrystalline cellulose | 30 |
| magnesium stearate | 2 |
|  | 330 mg | into a 9 mm tablet.

EXAMPLE B

An injection for parenteral administration was prepared from the following

|  | % w:w |
| --- | --- |
| Compound of Structure (1) | 50% (w:v) |
| 1 M citric acid | 30% (v:v) |
| sodium hydroxide (qs) | to pH 3.2 |
| water for injection EP | to 100 ml |

The compound of Structure (I) was dissolved in the citric acid and the pH slowly adjusted to pH 3.2 with the sodium hydroxide solution. The solution was then made up to 100 ml with water, sterilised by filtration and sealed into appropriately sized ampoules and vials.

Biological Dam.

A. H+K+ATPase Activity.

The effects of a single high concentration (100 μM) of a compound of structure (I) on K-stimulated ATPase activity in lyophilised gastric vesicles was determined. Preferred compounds of structure (I) were also tested over a range of concentrations to determine $IC_{50}$ values.

(i) Preparation of lyophilised gastric vesicles (H/K-ATPase).

Lyophilised gastric vesicles were prepared from pig fundic mucosa after the method of Keeling el. al. *Biochem.Pharmacol.*, 34, 2967, 1985).

(ii) K+-stimulated ATPase activity.

K+-stimulated ATPase activity was determined at 37° C. in the presence of the following: 10 mM Pipes/Tris buffer pH 7.0, 2 mM MgSO4, 1 mM KCl, 2 mM Na2ATP and 3–6 μg protein/ml lyophilised gastric vesicles. After incubation for 30 minutes, the inorganic phosphate hydrolysed from ATP was determined by the method of Yoda and Hokin (*Biochem. Biophys. Res. Commun.* 40, 880, 1970).

Compounds of structure (I) were dissolved in dimethylsulphoxide which up to the highest concentration used had no effect on K+-stimulated ATPase activity.

The effect of the highest concentration of each compound of structure (I) on the recovery of a standard amount of inorganic phosphate was also determined.

The $IC_{50}$ values obtained are shown in the following table:

| Compound | IC50 (μM) |
| --- | --- |
| 1 | 0.84 |
| 2 | 2.50 |
| 3 | 0.18 |
| 4 | 0.36 |
| 5 | 4.40 |
| 6 | 44% @ 100 |
| 7 | 0.82 |
| 8 | 2.10 |
| 9 | 2.20 |
| 10 | 2.40 |
| 11 | 2.10 |
| 12 | 2.40 |
| 13 | 4.00 |
| 14 | 2.70 |
| 15 | 0.06 |
| 16 | 0.04 |
| 17 | 3.50 |

B. Rat Lumen Perfused Stomach (pentagastrin stimulated gastric acid secretion).

Using a modification of the procedure described by Ghosh & Schild (*Br. J. Pharmacology*, 13, 54, 1958), the compounds of the following examples were found on i.v. administration at a concentration of 10 μmole/kg to cause an inhibition of pentagastrin stimulated gastric acid secretion as shown in the following table:

| Example No. | % inhibition |
| --- | --- |
| 1 | 61 |
| 2 | 67 |
| 3 | 88 |
| 4 | 63 |
| 5 | 46 |
| 7 | 74 |
| 8 | 76 |
| 9 | 55 |
| 10 | 68 |
| 11 | 77 |
| 12 | 57 |
| 13 | 49 |
| 14 | 79 |
| 15 | 70 |
| 16 | 91 |

What is claimed is:

1. A pharmaceutically acceptable salt form of a compound of the structure:

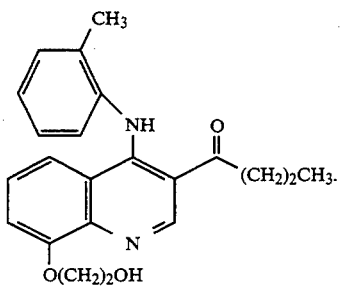

2. The salt according to claim 1 which is 3-butyryl-4-(2-methylphenylamino)-8-(2-hydroxyethoxy)quinoline hydrochloride.

3. The salt according to claim 1 which is 3-butyryl-4-(2-methylphenylamino)-8-(2-hydroxyethoxy)quinoline mesylate.

4. A pharmaceutical composition comprising a salt according to claim 1 and a pharmaceutically acceptable carrier or diluent.

5. A pharmaceutical composition comprising a compound according to claim 2 and a pharmaceutically acceptable carrier or diluent.

6. A pharmaceutical composition comprising a compound according to claim 3 and a pharmaceutically acceptable carrier or diluent.

7. A method of treatment of diseases caused or exacerbated by gastric acid which comprises administering to a subject in need thereof an effect amount of 3-butyryl-4-(2-methylphenylamino)-8-(2-hydroxy-ethoxy)-quinoline hydrochloride.

8. A method of treatment of diseases caused or exacerbated by gastric acid which comprises administering to a subject in need thereof an effect amount of 3-butyryl-4-(2-methylphenylamino)-8-(2-hydroxyethoxy)-quinoline mesylate.

9. A compound of the structure

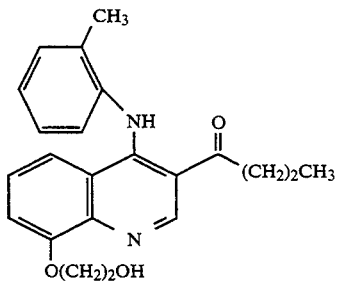

in the form of a salt, characterized in that the salt is that formed by reaction of the compound with a strong acid.

10. The compound according to claim 1 wherein the pharmaceutically acceptable salt is an acid addition salt.

* * * * *